United States Patent [19]

Mellul et al.

[11] Patent Number: 6,083,491
[45] Date of Patent: Jul. 4, 2000

[54] COSMETIC COMPOSITIONS CONTAINING A DISPERSION OF SOLID PARTICLES, THE SURFACE OF WHICH IS COATED WITH A CATIONIC POLYMER

[75] Inventors: Myriam Mellul, L'Hay les Roses; Didier Candau, Melun, both of France

[73] Assignee: L'Oreal, Paris, France

[21] Appl. No.: 08/117,128

[22] PCT Filed: Mar. 13, 1992

[86] PCT No.: PCT/FR92/00230

§ 371 Date: Dec. 8, 1993

§ 102(e) Date: Dec. 8, 1993

[87] PCT Pub. No.: WO92/16190

PCT Pub. Date: Oct. 1, 1992

[30] Foreign Application Priority Data

Mar. 14, 1991 [FR] France .................................. 91 03111

[51] Int. Cl.[7] .............................. A61K 7/02; A61K 7/027
[52] U.S. Cl. .............................. 424/63; 424/401; 424/64; 424/61
[58] Field of Search ................................ 424/63, 64, 401, 424/61

[56] References Cited

U.S. PATENT DOCUMENTS

| 3,761,418 | 9/1973 | Parran | 252/106 |
| 5,093,110 | 3/1992 | Kamen | 424/63 |
| 5,147,507 | 9/1992 | Gill | 162/158 |

FOREIGN PATENT DOCUMENTS

| 249685 | 12/1987 | European Pat. Off. . |
| 279319 | 8/1988 | European Pat. Off. . |
| 369741 | 5/1990 | European Pat. Off. . |
| 2234359 | 1/1975 | France . |
| 57903 | 8/1970 | Luxembourg . |

*Primary Examiner*—Sally Gardner-Lane
*Attorney, Agent, or Firm*—Nixon & Vanderhye, P.C.

[57] ABSTRACT

Skin or superficial body growth cosmetic composition containing a dispersion of solid particles in a binder, in which at least one part of said particles, especially the mineral filler and/or mineral pigments are introduced into said composition in the form of particles, the surface of which is coated with at least one cationic polymer. Said compositions are stable and are characterized, in particular, by a good stability and adhesion on the skin or integuments.

36 Claims, No Drawings

COSMETIC COMPOSITIONS CONTAINING A DISPERSION OF SOLID PARTICLES, THE SURFACE OF WHICH IS COATED WITH A CATIONIC POLYMER

The subject of the present invention is cosmetic compositions for the skin or superficial body growths, containing a dispersion of solid particles, into which are introduced solid particles whose surface is coated with a cationic polymer.

It is known that various makeup products such as loose or compacted powders, foundations, blushers, eye-shadows, makeup compositions for the eyelashes and eyebrows (for example mascaras), makeup compositions for the edge of the eyelids called eyeliners, as well as lipsticks are provided in the form of compositions comprising a dispersion of solid inorganic particles in a fatty binder. They may be anhydrous compositions or else oil-in-water or water-in-oil emulsions.

Depending on the types of compositions, the solid particles are either solely pigments (white and/or colored), intended to confer on the area of application (for example skin of the face or lips) a certain color, or particles, generally called "fillers", which have diverse functions varying with the nature of the particles.

In the compositions to be applied to the skin, there are often used fillers intended to provide a covering power, that is to say to mask the imperfections of the skin (differences in coloration, microreliefs) either by virtue of their opacity (such is the case especially for titanium and zinc oxides and for kaolin) or by their light-reflecting properties (such is the case especially for the lamellar fillers such as talc and micas). Fillers which are capable of absorbing the aqueous and oily secretions of the skin are also used in order to avoid the shiny appearance of the skin and the migration of the coloring materials: kaolin, starch, precipitated calcium carbonate, bentonite and the like are for example used for this purpose.

Micronized or non-micronized particles of $TiO_2$ and ZnO are also used as ultraviolet-absorbing agents.

In lipsticks, the solid particles dispersed in an appropriate fatty binder are especially colored pigments, optionally in combination with white pigments (for example fine particles of titanium dioxide) which make it possible to impart a shade to the colors provided by the colored pigments.

Such white and/or colored pigments are also used in nail varnish compositions which optionally consist of a dispersion of these pigments in a solution of a film-forming polymer and a plasticizer in an appropriate organic solvent.

The preparation and use of the cosmetic compositions containing dispersions of solid particles pose several types of problems. One problem common to the preparation of all the compositions which have just been discussed lies in the difficulty of obtaining stable dispersions, so as to apply, for example to the skin, a regular makeup whose application is uniform and which retains a good homogeneity. For this, specialists have been led to perform surface treatments on the powders used, especially in order to modify the interfacial properties involved in the wetting and dispersion phenomena. The aim of these treatments is often to render the powder hydrophobic in order to enhance its incorporation into the formulation binders and oils, and to increase the stability of the dispersion by reducing the phenomena of flocculation and aggregation; see for example European Patent 279 319 which describes the coating of pigments with siliconized polymers.

These treatments therefore make it possible to solve the problems of stability of the dispersion by limiting the flocculation phenomena. However, they do not solve another important problem, namely the weak properties of adhesion of the solid particles to the skin. Indeed, it is known that the solid particles used especially in the compositions in the form of powders have only weak properties of adhesion to the skin. The surface treatments intended to improve the stability of the dispersions in the fatty binders do not provide a substantial improvement as far as the adhesion properties are concerned.

It is known furthermore that the makeup products for the face and for the eyes are often provided in the form of compacted powders. The compacted powders are prepared by mixing the constituents of the powder with a binding agent, and then converted to the desired form by compression in appropriate containers.

The compacted powders should exhibit special characteristics of hardness. The hardness is a function of the applied compacting pressure. If the compacted product is too soft, it will be highly brittle and too large a quantity of product will be removed at the time of application. In contrast, if it is too hard, the disintegration will be difficult. Furthermore, a compact product should exhibit a perfectly flat surface. Finally, it should respond favorably to the drop test, that is to say exhibit a reduced loss of weight after a drop performed under specific conditions.

It has now been discovered that it is possible to obtain cosmetic compositions, comprising a dispersion of solid particles in a binder, having good properties of stability and adhesion to the skin or to superficial body growths, by introducing into the said compositions solid particles whose surface has been coated with a cationic polymer. It was observed, surprisingly, that the coating of the solid particles with cationic polymers, which nevertheless constitute a hydrophilic coating, does not prevent the obtaining of a good dispersibilty of the particles in the fatty binders. In addition, the compacted compositions obtained with cationic polymer-coated solid particles surprisingly exhibit good cohesion properties which result especially in a very satisfactory behavior in the drop tests. Furthermore, the compositions thus obtained have good properties of adhesion, for example to the skin or the hair, after application.

The subject of the present invention is therefore a cosmetic composition for the skin or superficial body growths, comprising a dispersion of solid particles in a binder, characterized by the fact that at least a portion of the said particles are introduced into the said composition in the form of particles whose surface is coated with at least one cationic polymer.

In the compositions of the invention, solid particles are superficially coated with a cationic polymer. This means that after coating, there is neither a change in morphology nor notable modification in the size of the particles, as verifiable by electron microscopy.

In the present application, the expression "cationic polymer" designates a polymer containing cationic groups or groups which can be ionized into cationic groups.

The preferred cationic polymers are chosen from those containing units comprising primary, secondary, tertiary and/or quaternary amine groups which may either form part of the polymer chain or be carried by a side substituent.

The cationic polymers used preferably have a molecular mass of between about $10^3$ and $3 \times 10^6$.

Preferably, the coated particles used in the compositions of the invention are coated solely with one (or more) cationic polymer(s).

The cationic polymers used are especially those containing at least 10% by weight of units comprising amine groups or quaternary ammonium groups whose quaternization value, expressed as cationic equivalent per gram of polymer, is for example at least equal to 0.05 cationic meq/g (meq: milliequivalent).

When the cationic polymer carries amine or quaternary ammonium groups carried by a side substituent, the polymer chain is for example an acrylic, vinyl, siliconized, fluorinated or saccharide chain.

Among the cationic polymers, there may be mentioned more particularly quaternized proteins, quaternized polysiloxanes, polyamine type polymers, polyaminoamide and quaternary polyammonium.

The quantities of polymer deposited on the particles vary with the procedure used for the coating. Generally, the proportion by weight of cationic polymer, relative to the total weight of the coated particles, is at least equal to 0.1%; the upper limit of the quantity of cationic polymer is sufficiently low for the particles to retain their individuality and their shape. In other words, the cationic polymer forms, at most, one thin (optionally lacunar) layer on the coated particles. Most often, the proportion by weight of cationic polymer in the coated particles is less than 10%, and preferably less than 8%, relative to the total weight of the coated particles.

The quaternized proteins are in particular chemically modified polypeptides carrying at the chain end, or grafted thereto, quaternary ammonium groups. Among these proteins, there may be mentioned especially:

hydrolysates of collagen carrying triethylammonium groups such as the products sold under the name QUAT-PRO E® by the company Maybrook and termed in the CTFA dictionary "Triethonium Hydrolyzed Collagen Ethosulfate", hydrolysates of collagen carrying trimethylammonium or trimethylstearylammonium chloride groups, sold under the name QUAT-PRO S® by the company Maybrook and termed in the CTFA dictionary "Steartrimonium Hydrolyzed Collagen";

hydrolysates of animal proteins carrying trimethylbenzylammonium groups such as the products sold under the name CROTEIN BTA® by the company Croda and termed in the CTFA dictionary "Benzyltrimonium hydrolyzed animal protein";

hydrolysates of proteins carrying on the polypeptide chain quaternary ammonium groups comprising at least one alkyl radical having 1 to 18 carbon atoms.

Among these protein hydrolysates, there may be mentioned inter alia:

CROQUAT L® whose peptide chain has a mean molecular weight of about 2,500 and whose quaternary ammonium group comprises a $C_{12}$ alkyl group;

CROQUAT M® whose peptide chain has a mean molecular weight of about 2,500 and whose quaternary ammonium group comprises a $C_{10}$–$C_{18}$ alkyl group;

CROQUAT S® whose polypeptide chain has a mean molecular weight of about 2,700 and whose quaternary ammonium group comprises a $C_{18}$ alkyl group;

CROTEIN Q® whose polypeptide chain has a mean molecular weight of the order of 12,000 and whose quaternary ammonium group comprises at least one alkyl group having 1 to 18 carbon atoms.

These different products are sold by the company Croda.

Other quaternized proteins are those corresponding to the formula:

(I)

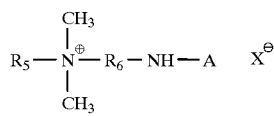

X⁻ is an anion of an organic or inorganic acid in which A designates a protein residue derived from hydrolysates of collagen protein, $R_5$ designates a lipophilic group comprising up to 30 carbon atoms, $R_6$ represents an alkylene group having 1 to 6 carbon atoms, these proteins have a molecular weight of between 1,500 and 10,000, preferably 2,000 and 5,000. There may be mentioned for example the products sold by the company Inolex, under the name LEXEIN QX 3000®, termed in the CTFA dictionary "Coco-trimonium Collagen Hydrolysate".

Among the quaternized proteins, there may also be mentioned quaternized plant proteins, such as wheat, maize or soya bean proteins; as quaternized wheat proteins, there may be mentioned those marketed by the company CRODA under the names HYDROTRITICUM WQ or QM®, termed in the CTFA dictionary "cocodimonium hydrolysed wheat protein", HYDROTRITICUM QL® termed in the CTFA dictionary "Laurdimonium hydrolysed wheat protein", or alternatively under the name HYDROTRITICUM QS® termed in the CTFA dictionary "Steardimonium hydrolysed wheat protein".

Another family of cationic polymers are the siliconized cationic polymers. Among these polymers, there may be mentioned (a) the quaternized polysiloxanes termed in the CTFA dictionary "Amodimethicone" and corresponding to the formula:

(II)

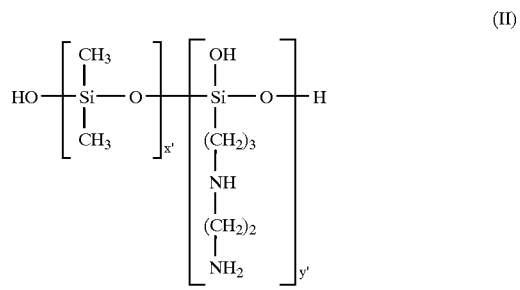

in which x' and y' are integers depending on the molecular weight which is generally between 5,000 and 10,000;

(b) the siliconized cationic polymers corresponding to the formula:

(III)

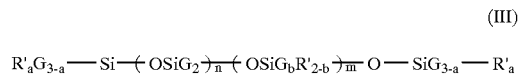

in which

G is a hydrogen atom or a phenyl or OH group or a $C_1$–$C_8$ alkyl, preferably methyl, group, a designates 0 or an integer from 1 to 3, and preferably 0, b designates 0 or 1 and preferably 1, the sum (n+m) is an integer from 1 to 2,000 and preferably from 50 to 150, it being possible for n to designate a number from 0 to 1,999 and preferably from 49 to 149 and it being possible for m to designate an integer from 1 to 2,000 and preferably from 1 to 10;

R' is a monovalent radical of formula $C_qH_{2q}L$ in which q is a number from 2 to 8 and L is chosen from the groups:

NR"—CH$_2$—CH$_2$—N(R")$_2$

N(R")$_2$ $^\oplus$N(R")$_3$A$^\ominus$ $^\oplus$N(R")H$_2$A$^\ominus$

NR"CH$_2$—CH$_2$—$^\oplus$NR"H$_2$A$^\ominus$;

NR"CH$_2$—CH$_2$—$^{\oplus NR"H}$$_2$A$^\ominus$ in which R" may designate hydrogen, phenyl, benzyl, a monovalent saturated hydrocarbon radical and preferably an alkyl radical having from 1 to 20 carbon atoms and A$^\ominus$ represents a halide ion such as fluoride, chloride, bromide or iodide.

A particularly useful product entering into this definition is the polymer termed "trimethylsilylamodimethicone" corresponding to the formula:

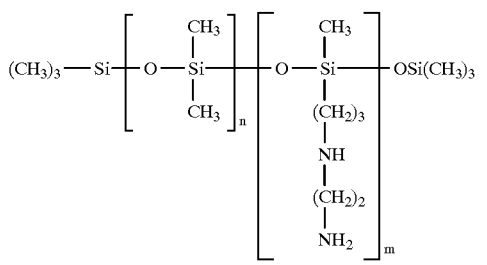

in which n and m have the meanings given above (of formula III). Such polymers are described in Patent Application EP-A-95238.

(c) the siliconized cationic polymers corresponding to the formula:

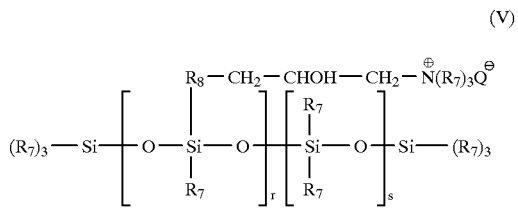

in which $R_7$ designates a monovalent hydrocarbon radical having from 1 to 18 carbon atoms and in particular an alkyl or alkenyl and, preferably, methyl radical;

$R_8$ designates a divalent hydrocarbon radical, preferably a $C_1-C_{18}$ alkylene radical or a $C_1-C_{18}$ and preferably $C_1-C_8$ divalent alkylenoxy radical;

$Q^-$ is a halide, preferably chloride, ion;

r represents a mean statistical value from 2 to 20 and preferably from 2 to 8;

s represents a mean statistical value from 20 to 200 and preferably from 20 to 50.

Such polymers are described more particularly in U.S. Pat. No. 4,185,087.

A polymer entering into this class is the polymer sold by the company Union Carbide under the name UCAR SILICONE ALE 56®.

When these siliconized polymers are used, a particularly advantageous embodiment is their simultaneous use with cationic surface-active agents, optionally non-ionic surface-active agents. There may be used for example in the compositions conforming to the invention the commercial product sold under the name EMULSION CATIONIQUE DC 929® by the company DOW CORNING which comprises, in addition to amodimethicone, a cationic surface-active agent corresponding to the formula:

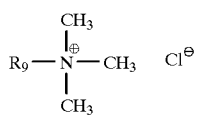

in which $R_9$ designates a mixture of alkenyl and/or alkyl radicals having from 14 to 22 carbon atoms, derived from tallow fatty acids, and a non-ionic surface-active agent of formula:

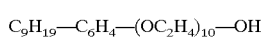

known under the name NONOXYNOL 10®.

Another composition which can be used in this embodiment of the invention is the composition containing the product sold under the name DOW CORNING Q2 7224® by the company Dow Corning comprising in combination the trimethylsilylamodimethicone of formula (IV), a non-ionic surface-active agent of formula:

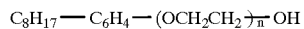

also termed octoxynol-40, another non-ionic surface-active agent of formula:

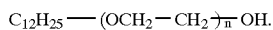

where n=6
also termed isolaureth-6, and glycol.

The polyamine, polyaminoamide and quaternary polyammonium type polymers which can be used in conformity with the present invention are described in particular in the Applicant's French Patent nos. 82 07 996 or 84 04 475. Among these polymers, there may be mentioned:

(1) the quaternized or non-quaternized vinylpyrrolidone-dialkylaminoalkyl acrylate or methacrylate copolymers such as the products sold under the name GAFQUAT® by the company GAP CORPORATION such as for example GAFQUAT 734® or 755® or alternatively the product termed COPOLYMERE 937®. These polymers are described in detail in French Patents 2,077,143 and 2,393,573.

(2) The cellulose ether derivatives comprising quaternary ammonium groups described in French Patent 1,492,597 and in particular the polymers marketed under the names "JR" (JR 400®, JR 125®, JR 30M®) or "LR" (LR 400®, LR 30 M®) by the company Union Carbide Corporation. These polymers are also defined in the CTFA dictionary as quaternary ammonium salts of hydroxyethyl cellulose having reacted with an epoxide substituted by a trimethylammonium group.

(3) The cationic cellulose derivatives such as the cellulose copolymers or the cellulose derivatives grafted with a water-soluble quaternary ammonium monomer and which are described in greater detail in U.S. Pat. No. 4,131,576 such as hydroxyalkyl celluloses like hydroxymethyl, hydroxyethyl or hydroxypropyl celluloses grafted with a salt of methacryloylethyl trimethylammonium, methacrylamidopropyl trimethylammonium or dimethyldiallylammonium.

The commercial products corresponding to this definition are more particularly the products sold under the name CELQUAT L 200® and CELQUAT H 100® by the company National Starch.

(4) The cationic polysaccharides described more particularly in U.S. Pat. Nos. 3,589,578 and 4,031,307 and more particularly the product marketed under the name JAGUAR C. 13 S® sold by the company Meyhall.

(5) The polymers consisting of piperazinyl units and straight or branched chain divalent alkylene or hydroxyalkylene radicals, optionally interrupted by oxygen, sulphur or nitrogen atoms or by aromatic or heterocyclic rings as well as the oxidation and/or quaternization products of these polymers. Such polymers are described in French Patents 2,162,025 and 2,280,361.

(6) The water-soluble polyaminopolyamides prepared in particular by polycondensation of an acidic compound with a polyamine. These polyaminoamides may be cross-linked by an epihalohydrin, a diepoxide, a dianhydride, an unsaturated anhydride, a bis-unsaturated derivative, a bis-halohydrin, a bis-azetidinium, a bis-haloacyldiamine, a bis-alkyl halide or alternatively by an oligomer resulting from the reaction of a bifunctional compound reactive towards a bis-halohydrin, a bis-azetidinium, a bis-haloacyldiamine, a bis-alkyl halide, an epihalohydrin, a diepoxide or a bis-unsaturated derivative; the cross-linking agent being used especially in proportions ranging from 0.025 to 0.35 mole per amine group of the polyaminopolyamide.

These polyaminopolyamides may be alkylated or if they comprise one or more quaternized tertiary amine functional groups. Such polymers are described in particular in French Patents 2,252,840 and 2,368,508.

(7) The polyaminopolyamide derivatives resulting from the condensation of polyalkylene polyamines with polycarboxylic acids followed by an alkylation using bifunctional agents. There may be mentioned for example the adipic acid-dialkylaminohydroxyalkyldialkylenetriamine polymers in which the alkyl radical comprises 1 to 4 carbon atoms and preferably designates methyl, ethyl or propyl. Such polymers are described in French Patent 1,583,363.

Among these derivatives, there may be mentioned more particularly the adipic acid/dimethylaminohydroxypropyl/diethylenetriamine polymers sold under the names CARTARETINE F, $F_4$ or $F_8$® by the company Sandoz.

(8) The polymers obtained by reaction of a polyalkylenepolyamine comprising two primary amine groups and at least one secondary amine group with a dicarboxylic acid chosen from diglycolic acid, and saturated aliphatic dicarboxylic acids having 3 to 8 carbon atoms. The mole ratio between the polyalkylenepolyamine and the dicarboxylic acid being between 0.8:1 and 1.4:1; the resulting polyaminopolyamide being reacted with epichlorohydrin in a mole ratio of epichlorohydrin to the secondary amine group of the polyaminopolyamide of between 0.5:1 and 1.8:1. Such polymers are described in particular in U.S. Pat. Nos. 3,227,615 and 2,961,347.

Polymers of this type are in particular marketed under the name HERCOSETT 57® by the company Hercules Incorporated or alternatively under the name PD 170® or DELSETTE 101® by the company Hercules in the case of the adipic acid/epoxypropyl/diethylenetriamine copolymer.

(9) The cyclopolymers having a molecular weight of 20,000 to 3,000,000 such as homopolymers comprising as principal constituent of the chain units corresponding to the formulae (IX) or (IX')

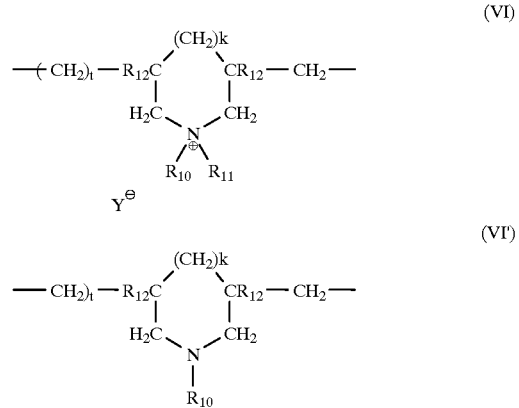

k and t are equal to 0 or 1, and the sum k+t-1, $R_{12}$ designates hydrogen or methyl, $R_{10}$ and $R_{11}$ designate independently of each other an alkyl group having from 1 to 22 carbon atoms, a hydroxyalkyl group in which the alkyl group preferably has 1 to 5 carbon atoms, a lower amidoalkyl group and where $R_{10}$ and $R_{11}$ may designate together with the nitrogen atom to which they are attached heterocyclic groups such as piperidyl or morpholinyl, as well as the copolymers comprising the units of formula (VI) or (VI') and units derived from acrylamide or diacetone acrylamide, $Y^\ominus$ is an anion such as bromide, chloride, acetate, borate, citrate, tartrate, bisulphate, bisulphite, sulphate and phosphate. Among the polymers defined above, there may be mentioned more particularly the dimethyldiallylammonium chloride homopolymer sold under the name MERQUAT 100® having a molecular weight of less than 100,000 and the dimethyldiallylammonium chloride and acrylamide copolymer having a molecular weight greater than 500,000 and sold under the name MERQUAT 550® by the company Merck.

These polymers are described more particularly in French Patent 2,080,759 and its certificate of addition no. 2,190,406.

(10) The quaternary polyammonium polymer containing recurring units corresponding to the formula:

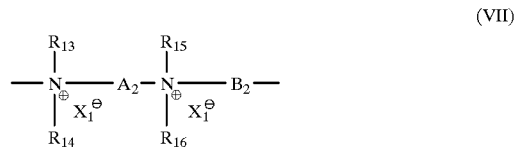

in which $R_{13}$ and $R_{14}$, $R_{15}$ and $R_{16}$ being identical or different, represent aliphatic, alicyclic or arylaliphatic radicals containing from 1 to 20 carbon atoms or low hydroxyalkylaliphatic radicals, or alternatively $R_{13}$ and $R_{14}$ and $R_{15}$ and $R_{16}$, together or separately, constitute with the nitrogen atoms to which they are attached, heterocycles optionally containing a second heteroatom other than nitrogen or alternatively $R_{13}$, $R_{14}$, $R_{15}$ and $R_{16}$ represent a linear or branched $C_2$–$C_6$ alkyl radical substituted by a nitrile, ester, acyl or amide group or a group

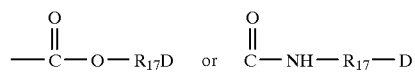

where $R_{17}$ is an alkylene and D a quaternary ammonium group.

$A_2$ and $B_2$ represent polymethylene groups containing from 2 to 20 carbon atoms which may be linear or branched, saturated or unsaturated and which may contain, bonded to or intercalated into the principal chain, one or more aromatic rings, or one or more oxygen or sulphur atoms or SO, $SO_2$, disulphide, amino, alkylamino, hydroxyl, quaternary ammonium, ureido, amide or ester groups and $X^e{}_1$ designates an anion derived from an inorganic or organic acid.

$A_2$ and $R_{13}$ and $R_{15}$ may form with the two nitrogen atoms to which they are attached, a piperazine ring; in addition, if $A_2$ designates a saturated or unsaturated, linear or branched alkylene or hydroxyalkylene radical, $B_2$ may also designate a group:

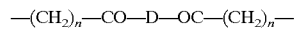

in which D designates:

a) a glycol residue of formula: O—Z—O— where Z designates a linear or branched hydrocarbon radical or a group corresponding to the formula:

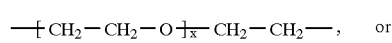

-continued $$\left[-CH_2-CH-O\right]_y-CH_2-CH-$$
$$\qquad\quad\;\;|\qquad\qquad\;\;\;|$$
$$\qquad\quad CH_3\qquad\quad\;CH_3$$

where x and y designate an integer from 1 to 4, representing a defined and unique degree of polymerization or any number from 1 to 4 representing a mean degree of polymerization;

b) a bis-secondary diamine residue such as a piperazine derivative, c) a bis-primary diamine residue of formula:

—NH—Y—NH— where Y designates a linear or branched hydrocarbon radical or alternatively the bivalent radical

—CH$_2$—CH$_2$—S—S—CH$_2$—CH$_2$— d) a ureylene group of formula:

—NH—CO—NH—;

$X^\ominus$ is an anion such as chloride or bromide.

These polymers have a molecular mass generally between 1,000 and 100,000.

Polymers of this type are described in particular in French Patents 2,320,330, 2,270,846, 2,316,271, 2,336,434 and 2,413,907 and U.S. Pat. No. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The quaternary polyammonium polymers consisting of the units of formula:

(VIII)

$$\left[\begin{array}{c}R_{18}\\|\\{}^\oplus N\text{-(}CH_2\text{)}_{\overline{x}}NH-\overset{O}{\overset{\|}{C}}\text{-(}CH_2\text{)}_{\overline{m}}\overset{O}{\overset{\|}{C}}-NH\text{-(}CH_2\text{)}_{\overline{y}}\overset{R_{20}}{\overset{|}{N}}{}^\oplus-A\\|\\R_{19}\quad X^\ominus\qquad\qquad\qquad\qquad\qquad R_{21}\end{array}\right]_{X^\ominus}$$

in which $R_{18}$, $R_{19}$, $R_{20}$ and $R_{21}$ which are identical or different, represent a hydrogen atom or a methyl, ethyl, propyl β-hydroxyethyl, β-hydroxypropyl or —CH$_2$CH$_2$(OCH$_2$CH$_2$)$_p$OH radical where p is equal to 0 or an integer between 1 and 6, provided that $R_{18}$, $R_{19}$, $R_{20}$ and $R_{21}$ do not simultaneously represent a hydrogen atom, x and y, which are identical or different, are integers between 1 and 6;

m is equal to 0 or an integer between 1 and 34,

X designates a halogen atom,

A designates the residue of a dihalide radical and preferably represents

—CH$_2$—CH$_2$—O—CH$_2$—CH$_2$—

Such compounds are described in greater detail in European Patent Application 122 324.

(12) The homopolymers or copolymers derived from acrylic or methacrylic acids comprising the units:

$$\begin{array}{ccc}\quad R_{24} & \quad R_{24}\\\quad| & \quad|\\-CH_2-C- , & -CH_2-C- \quad\text{or}\\\quad| & \quad|\\\quad C=O & \quad C=O\\\quad| & \quad|\\\quad O & \quad O\\\quad| & \quad|\\\quad A_1 & \quad A_1\\\quad| & \quad|\\\quad N & \quad R_{26}-\underset{|}{\overset{\oplus}{N}}-R_{27}\\/\;\backslash & \quad|\quad X_2^\ominus\\R_{22}\;R_{23} & \quad R_{25}\end{array}$$

$$\begin{array}{c}R_{24}\\|\\-CH_2-C-\\|\\C=O\\|\\NH\\|\\A_1\\|\\R_{26}-\underset{|}{\overset{\oplus}{N}}-R_{27}\\|\quad X_2^\ominus\\R_{25}\end{array}$$

in which $R_{24}$ designates H or CH$_3$. $A_1$ is a linear or branched alkyl group of 1 to 6 carbon atoms, or a hydroxyalkyl group of 1 to 4 carbon atoms, $R_{25}$, $R_{26}$, $R_{27}$, which are identical or different, represent an alkyl group having from 1 to 18 carbon atoms or a benzyl radical, $R_{22}$ and $R_{23}$ represent hydrogen or an alkyl group having from 1 to 6 carbon atoms. $X_2^\ominus$ designates a methosulphate anion or a halide such as chloride or bromide.

The comonomer(s) which can be used belongs(belong) to the family comprising: acrylamide, methacrylamide, diacetone acrylamide, acrylamide and methacrylamide which are nitrogen-substituted by lower alkyls, alkyl esters of acrylic or methacrylic acids, vinylpyrrolidone and vinyl esters.

13) The quaternary vinylpyrrolidone and vinylimidazole polymers such as for example the products marketed under the names LUVIQUAT FC 905®, FC 550® and FC 370° by the company BASF.

Other cationic polymers which can be used in conformity with the invention are polyalkyleneimines, in particular polyethyleneimines, polymers containing vinylpyridine or vinylpyridinium units, condensates of polyamines and epichlorohydrin, quaternary polyureylenes and chitin derivatives.

Among the cationic polymers which can be used in the compositions of the invention, there may be mentioned especially the following polymers:

the polymer comprising the units of formula:

$$\left[\begin{array}{c}CH_3\\|\\-\underset{|}{\overset{\oplus}{N}}-(CH_2)_3NH\overset{\|}{\underset{O}{C}}-(CH_2)_4-\overset{\|}{\underset{O}{C}}-NH-(CH_2)_3-\underset{|}{\overset{\oplus}{N}}-CH_2-CH_2-O-CH_2-CH_2\\CH_3\qquad\qquad\qquad\qquad\qquad\qquad\qquad\qquad\qquad CH_3\\X^\ominus\qquad\qquad\qquad\qquad\qquad\qquad\qquad\qquad\qquad\qquad X^\ominus\end{array}\right]$$

sold under the name MIRAPOL AD 1® by the company Miranol, the polymer comprising the units of formula:

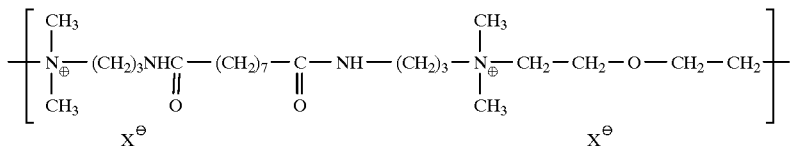

sold under the name MIRAPOL AZ1® by the company Miranol, poly(methacrylamidopropyltrimethylammonium chloride) sold under the name POLYMAPTAC® by the company Texaco Chemicals;

a quaternized polymer of the ionene type described in French Patent no. 2,270,846 and more particularly those comprising the units:

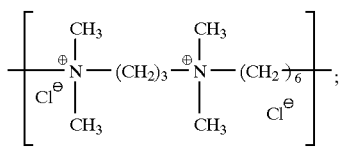

the dimethyldiallylammonium cyclopolymers sold under the names MERQUAT 100® and MERQUAT 550® by the company Merck;

the quaternary vinylpyrrolidone and vinylimidazole polymers such as those sold under the names LUVIQUAT FC 905®, FC 550® and FC 370® by the company BASF the quaternized or non-quaternized vinylpyrrolidone/dialkylaminoalkyl acrylate or methacrylate copolymers such as the products sold under the names COPOLYMERE 937®, GAFQUAT 734® or 755® by the company GAF;

the quaternary cellulose ether polymers such as those sold under the names "JR" such as for example JR 125®, JR 400®, JR 30-M ® and LR such as LR 400® and LR 30® by the company Union Carbide Corporation;

the cationic cellulose derivatives such as the products sold under the names CELQUAT L 200® and CELQUAT H 100® by the company National Starch;

the quaternary ammonium polymers of the type described in U.S. Pat. No. 4,157,388 and more particularly the polymer comprising units of formula:

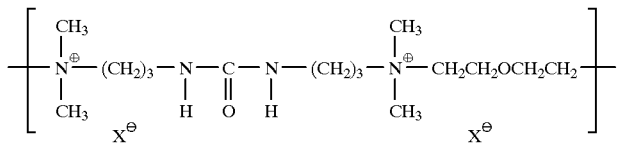

sold under the name MIRAPOL A 15® by the company Miranol;

poly(dimethylbutenylammonium chloride)-α, ω-bis (triethanolammonium chloride) sold under the name ONAMER M® by the company Onyx Internationale.

the amine-containing polymers with siliconized skeleton such as the amodimethicone contained in the cationic emulsion DC929® marketed by Dow Corning.

The coated particles present in the composition of the invention preferably comprise inorganic fillers or pigments.

The natural or synthetic inorganic fillers are for example chosen from: calcium carbonates, silicates such as for example aluminium silicate or kaolin, calcium silicates, sodium aluminosilicate, magnesium silicate or talc, potassium aluminosilicates or micas and hydrated magnesium aluminosilicate; sulphates such as for example barium sulphate, calcium sulphate; precipitated or pyrogenic silicon dioxides, as well as silica hydrogels and aerogels.

The pigments are chosen for example from white pigments such as titanium dioxide or zinc oxide and colored pigments such as: colored iron oxides (natural or synthetic) black, red and yellow in color; hydrated or non-hydrated green chromium oxides; Prussian blue; sodium aluminosulphosilicates and their different variants known under the name of "ultramarine" pigments; cobalt aluminate or cobalt blue and manganese violet.

The pigments may also be:

either pearly pigments such as mica-titaniums (mica coated with particles of titanium dioxide) and bismuth oxychloride;

or micronized pigments of metallic oxides chosen from titanium, zinc, cerium or zirconium oxides or mixtures thereof.

The starting pigments intended to be coated with a cationic polymer in conformity with the invention may be pigments having undergone one or more surface treatments of chemical, electronic, mechanicochemical and/or mechanical nature with compounds as described for example in Cosmetics & Toiletries, February 1990, Vol. 105, p. 53–64, especially with amino acids, beeswax, fatty acids, fatty alcohols, anionic surface-active agents, lecithins, sodium, potassium, zinc, iron or aluminum salts of fatty acids, metallic alkoxides (of titanium or aluminum), polyethylenes, silicones, proteins (collagen, elastin), alkanolamines, silicon oxides, metallic oxides or sodium hexametaphosphate.

In the compositions of the invention, the proportions of coated particles dispersed in the binder depend on the type of compositions; the proportions are customary for the type of composition considered.

In order to coat the particles, a known method, for example one of the following methods, may be used:

1) A solution of the polymer is prepared in one of its good solvents. The powder to be coated is dispersed in this solution with vigorous stirring and a poor solvent for the polymer is added without proceeding up to the precipitation of the polymer in the solution, but up to the first cloudiness.

The suspension is then left vigorously stirred, for example for 4 hours. The suspension is allowed to settle, it is rinsed with a non-solvent of the polymer and dried, for example at 80° C. under reduced pressure.

2) A solution of the polymer is prepared in which the powder to be coated is dispersed. The system is left vigorously stirred and a precipitant of the polymer is slowly added so as to gently precipitate the polymer at the surface of the powder. The mixture is allowed to settle, it is rinsed with a non-solvent of the polymer and the powder is dried.

3) A solution is prepared with a good solvent of the polymer and the powder to be coated is dispersed therein. A poor solvent of the polymer is chosen whose boiling point is greater than that of the good solvent and a slow evaporation of the system is carried out. This results in the formation of a coacervate which gradually coats the powder, and then the powder is dried.

4) The so-called fluidized bed technique is used: a dilute solution of the polymer is sprayed hot in a cyclone in which the powder is kept in sustentation.

5) A solution of the polymer is prepared in which the powder to be coated is dispersed. The system is left vigorously stirred and the solvent is evaporated slowly so as to gently precipitate the polymer at the surface of the powder. It is allowed to settle, rinsed with a non-solvent of the polymer and the powder is dried.

6) Spray-drying process:
A solution of the polymer is prepared in which the powder to be coated is dispersed. The solution is aspirated by means of a pump and it is sent into a heating channel where the solvent is evaporated. The coated powder is recovered by means of an aspirator into a cyclone.

7) Freeze-drying process:
A solution of the polymer is prepared in which the powder to be coated is dispersed. The mixture is frozen and it is placed under vacuum. The coated product is then recovered.

The compositions of the invention may be anhydrous compositions. The anhydrous compositions are provided especially in the form of a compacted powder, a cast powder, a lipstick or a nail varnish.

The compositions of the invention may also be provided in the form of water-in-oil or oil-in-water type emulsions and may be used as foundation or mascara for example.

These compositions are prepared according to the customary methods.

In the makeup compositions, the binder is a customary fatty binder consisting of an oil, a mixture of oils or a mixture of oil and wax(waxes).

In the lipsticks, the binder is also a fatty binder generally consisting of a mixture of (natural or synthetic) waxes of high melting point, (synthetic, mineral or vegetable) oils and (natural or synthetic) waxes of low melting point.

In the nail varnishes, the binder consists of the solution of the film-forming polymer and the plasticizer in the chosen organic solvent.

In the emulsions, the binder is especially a customary fatty binder consisting for example of an oil or a mixture of oils.

When the composition comprises a micronized pigment of metallic oxides chosen from titanium, zinc, cerium or zirconium oxides or mixtures thereof, it may constitute a composition for protecting the human epidermis against ultraviolet rays.

The invention also relates to the use, in the preparation of a cosmetic composition, containing a dispersion of solid particles in a binder, of particles whose surface is coated with at least one cationic polymer. In this use, the composition, and especially the particles, the cationic polymer, as well as the binder, are in particular as defined above.

The invention relates, in addition, to a process of cosmetic treatment, characterized by the fact that a cosmetic composition as defined above is applied to the skin or superficial body growths.

The application of the compositions of the invention is carried out in the customary manner and quantity.

The following examples illustrate the invention without however limiting it.

PREPARATION EXAMPLE 1

30 g of a copolymer of vinylpyrrolidone and diethyl sulphate-quaternized dimethylaminoethyl methacrylate, containing 80% by weight of vinylpyrrolidone units (GAFQUAT 755N from the company GAF), are introduced into 100 ml of water.

A dispersion of 75 g of talc is prepared in parallel in 230 g of water. When a correct dispersion is obtained, the latter is poured into the copolymer solution and it is left stirring for 4 hours. 710 ml of acetone are then added and the mixture is again left stirring for 4 hours. The preparation is allowed to settle, the talc is recovered, rinsed with acetonitrile, dried, ground and sifted. Elemental analysis of the organic residue shows that a coated powder has been obtained containing 2.41% by weight of the cationic polymer.

In a similar manner, chromium oxide and mica-titaniums were coated:

chromium oxide marketed by Whittaker under the name ULTRA GREEN BC 710®;

mica-titanium 31/69 marketed by Mearl under the name FLAMENCO SATINA®;

mica-titanium 83/17 marketed by Mearl under the name TIMACA SPARKLE®.

PREPARATION EXAMPLE 2

150.9 g of a methacrylamidopropyltrimethylammonium chloride polymer are dissolved in 1300 ml of water. A dispersion of 500 g of talc is prepared in parallel in 1500 ml of water. The dispersion is added to the polymer solution and the mixture is left stirring for 4 hours. The powder is recovered by centrifugation and the pellet is rinsed with 500 ml of acetonitrile and then dried, ground and sifted.

The cationic polymer used is POLYMAPTAC®, marketed by the company Texaco Chemicals. The coated talc contains 2% of the cationic polymer.

In a similar manner, chromium oxide and mica-titaniums were coated.

PREPARATION EXAMPLE 3

The procedure is carried out in a manner similar to that described in Example 1, with 82.8 g of cationic polymer in 1500 ml of water. The powder obtained after settling has taken place is rinsed with 2600 ml of isopropanol.

The cationic polymer used is the MEXOMERE PO® marketed by the company Chimex. It is a polymer which results from the condensation of N,N'-tetramethylpropylenediamine with 1,6-dichlorohexane.

The proportion of cationic polymer in the coated talc is 5%.

In a similar manner, chromium oxide and micatitaniums were coated.

PREPARATION EXAMPLE 4

142.3 g of a siliconized cationic polymer carrying a side chain terminating in a primary amine functional group (amodimethicone contained in the emulsion DC 929® from Dow Corning) are used as starting material. This emulsion is diluted with 1400 ml of water.

A dispersion of talc is prepared in parallel by introducing 500 g of talc into 1500 ml of water.

The dispersion thus prepared is added to the siliconized polymer emulsion and left stirring for 4 hours. The water is then distilled off so as to bring about the coalescence of the emulsion and the adsorption of the polymer on the talc.

The product is rinsed with water, dried in a vacuum oven, ground and sifted. The coated talc contains 3% of the cationic polymer.

PREPARATION EXAMPLE 5

250 g of a poly(ethyleneimine), cationic polymer which contains secondary and primary amine functional groups, are introduced into 1400 ml of water.

A dispersion of talc is prepared in parallel by introducing 500 g of talc into 1600 ml of water.

The talc dispersion is introduced into the polymer solution and the mixture is left stirring for 4 hours.

The coated talc is recovered and is rinsed with acetonitrile and then dried in an oven, ground and sifted. It contains 0.4% of the cationic polymer.

The poly(ethyleneimine) used is marketed under the name POLYMINE SK® by the company BASF.

PREPARATION EXAMPLE 6

Coating by spray-drying 1.66 g of MEXOMERE PO® polymer in solution at 60% by weight in water are dissolved in 400 ml of water and 100 g of micronized titanium dioxide are dispersed therein. The mixture should be sufficiently fluid (water is added if necessary). The mixture is left stirring for 1 hour and the spray-drying is then carried out by means of the BUCHI 190®—Mini Spray Dryer apparatus.
Operating conditions
 Flow rate: 600–700
 Inlet temperature: 130° C. (graduation 10)
 Outlet temperature: 60° C.
 Aspirator: 20
 Pump: 10

During the entire spray-drying, the mixture is kept magnetically stirred.

A product with a very fine feel is recovered which does not need to be sifted or dried. The coated titanium dioxide contains 1% of the cationic polymer.

PREPARATION EXAMPLE 7

Coating by freeze-drying 0.606 g of POLYMAPTAC® polymer in solution at 33% by weight in water is dissolved in 50 ml of water and 10 g of talc are incorporated with magnetic stirring. The mixture is left magnetically stirring for 5 hours.

The mixture is poured into a 600 ml container, it is frozen by means of liquid nitrogen and then it is placed in the modular freeze dryer VIRTIS®—model 10 020 for at least 18 hours.

A fairly pulverulent product is recovered which is sifted on 100 μm. The coated talc contains 2% of the cationic polymer.

PREPARATION EXAMPLE 8

The procedure is carried out in a manner similar to that described in Example 7, with 0.893 g of quaternized wheat protein sold under the name HYDROTRITICUM WQ® by the company Croda (in solution at 28% by weight in water) in 50 ml of water and 10 g of talc.

A fairly pulverulent product is recovered which is sifted on 100 μm.

The coated talc contains 2.5% of the cationic polymer.

EXAMPLES OF COMPOSITIONS

EXAMPLE A

Formulation of an eyeshadow

| Talc treated according to the invention* | 40% |
|---|---|
| Anhydrous chromium oxide | 15% |
| Mother-of-pearl (mica-titanium) | 35% |
| Fatty binder | 10% |

*according to Preparation Example 1

This cosmetic preparation is produced according to a conventional formulation procedure using a Baker-Perkin type decaking agitator. The mother-of-pearl is introduced after mixing the powders. When the mixture is homogeneous, the fatty binder is added with reduced stirring. This binder consists of:

| Oleyl alcohol | 11% |
|---|---|
| Vaseline | 11% |
| Paraffin oil | 67% |
| Isopropyl myristate | 11% |

A sensory evaluation test was performed on the cosmetics thus prepared. For this, a group of 25 testers was formed who evaluated these cosmetics according to an assessment criterion which is the ability to make streaks. The test consists in applying the test formula to the eyelids. The result is judged immediately after application and 4 hours later. When a formula exhibits good adhesion to the skin, the makeup remains uniform several hours after application. When the adhesion is poor, streaks appear which separate the areas where the makeup adheres from those where the makeup has become detached from the skin. The formulas using coated talcs according to the invention were always judged to be much superior to those using uncoated talcs.

EXAMPLE B

Compacted eyeshadows—Study of the mechanical properties

FORMULATION

Compacted (hereinbelow: "compacts") eyeshadows were prepared according to the formulations indicated in Table 1 below.

The binder is that described in Example A below.

DROP TEST

The compact is subjected to 9 successive drops at a height of 20 cm. The loss in weight of the compact is noted after 9 drops.

TEST OF HARDNESS

The hardness is measured with a durometer of ZWICK® brand.

It is expressed in degrees Shore.

Generally, a balance is sought which makes it possible to obtain a compact which can disintegrate (in order to remove the product and apply it) but which is sufficiently hard so as to exhibit a good solidity and be able to be handled without special precautions and without loss of product.

The hardness is a function of the compacting pressure which makes it possible to obtain products which give a minimum loss in the drop test.

The results are collated in Table 1 below.

Compacting pressures:
 60 b (60 bar):$6 \times 10^6$ Pa
 40 b (40 bar):$4 \times 10^6$ Pa
 30 b (30 bar):$3 \times 10^6$ Pa

TABLE 1

|  | Control |  | Mexomère PO ® coating according to Example 3 |  | PolyMAPTAC coating according to Example 2 |  | GAFQUAT ® coating according to Example 1 |  |
| --- | --- | --- | --- | --- | --- | --- | --- | --- |
| Talc |  | 40% | Treated talc | 40% | Treated talc | 40% | Treated talc | 40% |
| Chromium oxide |  | 15% | Treated chromium oxide | 15% | Treated chromium oxide | 15% | Treated chromium oxide | 15% |
| Mica-titanium 31/69 |  | 20% | Treated mica-titanium 31/69 | 20% | Treated mica-titanium 31/69 | 20% | Treated mica-titanium 31/69 | 20% |
| Mica-titanium 83/17 |  | 15% | Treated mica-titanium 83/17 | 15% | Treated mica-titanium 83/17 | 15% | Treated mica-titanium 83/17 | 15% |
| Binder |  | 10% | Treated binder | 10% | Binder | 10% | Binder | 10% |
| Compacting: 60 b/2.9 g | | | Compacting 30 b/2.7 g 60 b/3 g | | Compacting 30 b/3 g 60 b/3 g | | Compacting 30 b/3 g 60 b/3 g | 40 b/3 g |
| Hardness: 38 | | | Hardness 29 33.8 | 21.8 | Hardness 43.7 | 32.3 | Hardness 56.7 | 49.5 |
| Drops (weight loss %) 5.80% | | | Drops (weight loss %) 0% | 21.6% | Drops (weight loss %) 0% | 0.11% | Drops (weight loss %) 0.33% | 1.06% |

EXAMPLE 2

Foundation

A foundation having the following formulation is prepared in the form of a water-in-oil emulsion:

| | | |
|---|---|---|
| A | Cetyl dimethicone copolyol* | 5.00% |
| | Cyclomethicone** | 5.00% |
| | Isostearic acid glycerides esterified by succinic acid | 2.00% |
| | Modified clay*** | 10.00% |
| B | Glycerol | 15.00% |
| | Preservative | 0.50% |
| | Magnesium sulphate | 0.50% |
| | Water | 46.80% |
| C | Caprylic and capric acid triglycerides | 4.00% |
| | Dimethiconol in cyclomethicone**** | 16.00% |
| | Treated yellow iron oxide | 1.43% |
| | Treated red iron oxide | 0.55% |
| | Treated black iron oxide | 0.22% |
| | Treated titanium dioxide | 4.80% |

*marketed under the name ABIL WE 0.9 ® by goldschmidt.
**marketed under the name VOLATILE SILICONE 7158 ® by Union Carbide
***SIMAGEL SI 345 ®(Dubois stearin factory)
****Q2 1401 ® sold by Dow Corning.

To prepare this foundation, the procedure is as follows:

The set B is added to the set A at 70° C. with stirring. Once the emulsion has formed, the mixture C is added.

The treated pigments were coated with GAFQUAT 755 N®, according to the procedure of Example 1.

EXAMPLE D

Foundation

A foundation having the following formulation is prepared in the form of an oil-in-water emulsion:

| | | |
|---|---|---|
| A | Water | 52.50% |
| | Acrylic acid/$C_{10}$–$C_{30}$ alkyl acrylate copolymer* | 0.10% |
| | Carboxyvinyl poplymer CARBOPOL 940 ® from goodrich) | 0.60% |
| | Triethanolamine | 0.80% |
| | Treated yellow iron oxide | 1.43% |
| | Treated red iron oxide | 0.55% |
| | Treated black iron oxide | 0.22% |
| | Treated titanium dioxide | 4.80% |

-continued

| | | |
|---|---|---|
| B | Glycerol | 2.00% |
| | Preservatives | 0.20% |
| | Water | 20.80% |
| C | Dimethiconol in cyclomethicone** | 16.00% |

*PEMULEN TR2 ® (goodrich)
**sold by DOW CORNING under the name Q2 1401.

To prepare this foundation, the procedure is as follows:

The mixture A is prepared at 70° C. by means of a dispersing device. The set B is added, still at high temperature. The emulsion is prepared by adding the set C to the A+B mixture while maintaining the stirring until the temperature returns to room temperature.

The treated pigments are pigments which were subjected to a coating treatment as described in Example 1.

EXAMPLE E

Nail varnish

Formulation:

| | | |
|---|---|---|
| A | Nitrocellulose | 14.90% |
| | Butyl acetate | 26.00% |
| | Ethyl acetate | 8.20% |
| B | Modified clay | 1.00% |
| | Anhydrous alcohol | 8.00% |
| | Santolite** resin | 7.10% |
| | Camphor | 2.40% |
| | Dibutyl phthalate | 4.80% |
| | Toluene | 26.00% |
| | Citric acid | 0.50% |
| C | Treated iron oxide* | 0.23% |
| | Titanium dioxide | 0.66% |
| | D & C pigment no. 5 | 0.08% |
| | D & C pigment no. 7 | 0.08% |
| | D & C pigment no. 34 | 0.05% |

*Iron oxide: treated as described in Example 1.
**Toluenesulphonamide-formaldehyde resin (Santolite).

To prepare this nail varnish, the procedure is carried out constantly at room temperature and with stirring. Mixtures A and B are prepared separately. A is added to B and then the set C consisting of the pigments is added.

In Examples F, G, H below, the eyeshadows are prepared in a manner similar to Example A by introducing the iron oxides after mixing the powders.

EXAMPLE F

Eyeshadow

| | |
|---|---|
| Talc | 22.9 g |
| Treated mica | 22.0 g |
| Bismuth oxychloride | 8.0 g |
| Titanium dioxide | 2.0 g |
| Zinc stearate | 3.0 g |
| Nylon powder sold under the name ORGASOL ® by the company Atochem | 20.0 g |
| Black iron oxide | 6.0 g |
| Red iron oxide | 6.5 g |
| Yellow iron oxide | 3.0 g |
| Fatty binder | 6.5 g |

The mica is coated with GAFQUAT 755 N®, according to the procedure of Example 1.

The binder is that described in Example A above.

EXAMPLE G

Eyeshadow

| | |
|---|---|
| Treated talc | 23.36 g |
| Treated mica | 22.44 g |
| Bismuth oxychloride | 8.0 g |
| Titanium dioxide | 2.0 g |
| Zinc stearate | 3.0 g |
| Nylon powder sold under the name ORGASOL ® by the company Atochem | 20.0 g |
| Treated black iron oxide | 6.12 g |
| Treated red iron oxide | 6.63 g |
| Treated yellow iron oxide | 3.06 g |
| Fatty binder | 5.29 g |

The treated pigments are coated with POLYMAPTAC® according to the procedure of Example 7.

The binder is that described in A above.

EXAMPLE H

Eyeshadow

| | |
|---|---|
| Treated talc | 24.045 g |
| Mica | 22.0 g |
| Bismuth oxychloride | 8.0 g |
| Titanium dioxide | 2.0 g |
| Zinc stearate | 3.0 g |
| Nylon powder sold under the name ORGASOL ® by the company Atochem | 20.0 g |
| Treated black iron oxide | 6.3 g |
| Treated red iron oxide | 6.825 g |
| Treated yellow iron oxide | 3.15 g |
| Fatty binder | 4.58 g |

The treated pigments are coated with MEXOMERE PO® according to the procedure of Example 6.

The binder is that described in Example A above.

A sensory evaluation test was carried out in a manner similar to that described in Example A, involving 16 people, with Examples F, G and H which were compared to a formula according to Example F in which the pigments were not coated. The formulas using coated pigments according to the invention were consistently judged superior to those using uncoated pigments.

EXAMPLE I

Cast blusher

| | | |
|---|---|---|
| A | Glycerol trilaurate | 2.23 g |
| | Acrylic acid and ethylene copolymer sold under the name A-C COPOLYMERE 540 ® by the company Allied | 9.81 g |
| | Vaseline | 7.15 g |
| | Lanolin alcohol | 3.06 g |
| B | Isostearyl neopnetanoate | 17.17 g |
| | Octyldodecanol | 9.42 g |
| | Mixture of octyl stearate and octyl palmitate sold under the name ESTAMOL EH 16/18 ® by the comapny DS Industrie | 18.84 g |
| C | Dimethicone sold under the name SILBIONE ® by the comapny Rhone Poulenc | 0.31 g |
| | Aluminum salt of the reaction product of octenyl succinic anhydride with starch sold under the name DRY FLO ® by the company National Starch | 15.27 g |
| | Mixture of mica and titanium dioxide sold under the name FLAMENCO SUPERPEARL ® by the company Mearl | 9.00 g |
| D | Titanium dioxide | 4.00 g |
| | Treated black iron oxide | 0.5 g |
| | Treated red iron oxide | 2.84 g |
| | Treated yellow iron oxide | 0.4 g |

The iron oxides are coated with GAFQUAT 755 N® according to the procedure of Example 1. The mixture D is ground in the mixture B. The mixture A is added. The whole is heated to 80–90° C. while stirring in order to homogenize. C is added. The mixture is cast hot into a dish.

EXAMPLE J

Mascara

| | | |
|---|---|---|
| A | Stearic acid | 6.0 g |
| | Glycerol stearate | 3.665 g |
| | Beeswax | 5.495 g |
| | Carnauba wax | 1.875 g |
| | Paraffin | 7.5 g |
| | Rosin (CTFA name) | 1.83 g |
| | Propylparaben | 0.05 g |
| B | Treated green chromium oxide | 6.10 g |
| | Mixture of ultramarines and treated silica (sold under the name BLEU D'OUTREMER SPECIAL ® by the company Wackherr) | 0.90 g |
| | Titanium dioxide | 0.50 g |
| C | Water | 56.799 g |
| | Methylparaben | 0.23 g |
| | Hydroxyethylcellulose sold under the name CELLOSIZE OP 4400 H ® by the company Amerchol | 0.22 g |
| | Triethanolamine | 3.0 g |
| | Pulverized gum arabic sold by the company Alland Robert | 5.836 g |

The treated pigments are coated with POLYMAPTAC® according to the procedure of Example 7.

The mixture A is heated to 90° C.

B is added to it and then the aqueous phase C, heated to 70–80° C., is added.

The mixture is stirred for 10 to 15 minutes in order to obtain the emulsion and it is allowed to cool.

An oily mascara is thus obtained having a fine dispersion of pigments.

EXAMPLE K

Composition for protecting the human epidermis

| | | |
|---|---|---|
| A | Mixture of glycerol stearate and polyethylene glycol stearate containing 100 ethylene oxide units sold under the name ARLACEL 165 ® by the company ICI | 1 g |
| | Vaseline oil | 15 g |
| | Stearic acid | 2 g |
| | Glycerine | 3 g |
| | Titanium dioxide treated with sodium hexametaphosphate (sold under the name MT 150W ® by the company Tayca) which is coated | 10.5 g |
| B | Cetyl alcohol and hydroxyethyl cellulose ether sold under the name NATROSOL PLUS Grade 330 CS ® by the company Aqualon | 0.5 g |
| | Preservatives qs | |
| | Perfume qs | |
| | Water qs | 100 g |

The titanium dioxide is 5% coated with GAFQUAT 755 N®, according to the procedure of Example 1.

The mixture A is heated to 80° C. and the mixture B is added at 80° C. The mixture is allowed to cool with stirring.

A water-in-oil emulsion for protecting the human epidermis against ultraviolet radiation is thus obtained.

We claim:

1. An anhydrous cosmetic composition for the skin consisting of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as a part of the polymer chain or as a side substituent, said fatty binder being at least one of an oil, a wax or a mixture thereof.

2. The cosmetic composition of claim 1 wherein said solid coated particles contain less than 8 percent by weight of cationic polymer.

3. The cosmetic composition of claim 1 wherein said coated particles comprise an inorganic filler or an inorganic pigment.

4. The cosmetic composition of claim 1 wherein said cationic polymer is an acrylic, vinyl, siliconized, fluorinated or saccharide polymer.

5. The composition of claim 3 wherein said inorganic filler is selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide and an aerogel.

6. The composition of claim 3 wherein said inorganic pigment is selected from the group consisting of titanium dioxide, zinc oxide, a colored natural or synthetic black iron oxide, a colored neutral or synthetic red iron oxide, a colored natural or synthetic yellow iron oxide, a hydrated green chromium oxide, a non-hydrated green chromium oxide, Prussian blue an ultramarine pigment, a cobalt aluminate, cobalt blue and manganese violet.

7. The composition of claim 3 wherein said inorganic pigment is selected from the group consisting of a mica-titanium and bismuth oxychloride.

8. The composition of claim 3 wherein said inorganic pigment is selected from the group consisting of zinc oxide, cerium oxide, zirconium oxide and mixtures thereof.

9. An anhydrous nail varnish composition consisting of a dispersion of solid particles in a binder comprising a solution of a film forming polymer and a plasticizer in an organic solvent, at least a portion of said solid particles having a solid surface coated with one or more cationic polymer present in an amount of from 0.1 percent to 10 percent by weight, relative to the total weight of said coated particles; said cationic polymer containing quaternary ammonium groups as a part of the polymer chain or as a side substituent.

10. The cosmetic composition of claim 9 wherein said coated particles comprise an inorganic filler or an inorganic pigment.

11. The cosmetic composition of claim 9 wherein said cationic polymer is an acrylic, vinyl, siliconized, fluorinated or saccharide polymer.

12. The composition of claim 10 wherein said inorganic filler is selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide, silica hydrogel and an aerogel.

13. The composition of claim 10 wherein said inorganic pigment is selected from the group consisting of titanium dioxide, zinc oxide, a colored natural or synthetic black iron oxide, a colored natural or synthetic red iron oxide, a colored natural or synthetic yellow iron oxide, a hydrated green chromium oxide, a non-hydrated green chromium oxide, Prussian blue, a sodium aluminosulphosilicate, an ultramarine pigment, a cobalt aluminate, cobalt blue and manganese violet.

14. The composition of claim 10 wherein said inorganic pigment is selected from the group consisting of a mica-titanium and bismuth oxychloride.

15. The composition of claim 10 wherein said inorganic pigment is selected from the group consisting of zinc, cerium, a zirconium pigment and a mixture thereof.

16. A cosmetic makeup process for the skin consisting of applying to the skin an anhydrous composition for the skin consisting essentially of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quatenary ammonium groups as a part of the polymer chain or as a side substituent, said fatty binder being at least one of an oil, a wax or a mixture thereof.

17. An anhydrous cosmetic composition for the skin consisting of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as a part of the polymer chain or a side substituent, said fatty binder being at least one of an oil, a wax or a mixture thereof, said composition being in the form of a compacted powder, a cast powder or a lipstick.

18. The cosmetic composition of claim 17, in the form of a lipstick.

19. A cosmetic treatment process for coloring lips, consisting essentially of applying to said lips an anhydrous cosmetic composition for the skin consisting essentially of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as a part of the polymer chain or a side substituent, said fatty binder being at least one of an oil, a wax or a mixture thereof, said composition being in the form of a lipstick.

20. The cosmetic composition of claim 17, in the form of a compacted power.

21. A cosmetic makeup process for coloring the skin and masking the imperfections thereof, consisting essentially of applying to said skin an anhydrous cosmetic composition for the skin consisting essentially of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as a part of the polymer chain or a side substituent, said fatty binder being at least one of an oil, a wax or a mixture thereof, said composition being in the form of a compacted powder.

22. A cosmetic treatment process for coloring nails consisting essentially of applying to said nails an anhydrous nail varnish composition consisting essentially of a dispersion of solid particles in a binder comprising a solution of a film forming polymer and a plasticizer in an organic solvent, at least a portion of said solid particles having a solid surface coated with at least one cationic polymer present in an amount of from 0.1 percent to 10 percent by weight, relative to the total weight of said coated particles; said cationic polymer containing quaternary ammonium groups as a part of the polymer chain or as a side substituent.

23. An anhydrous cosmetic composition for the skin consisting of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as part of the polymer chain or as a side substituent, wherein said solid particles are at least one of an inorganic filler selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide, an aerogel, and an inorganic pigment selected from the group consisting of titanium dioxide, zinc oxide, a colored natural or synthetic black iron oxide, a hydrated green chromium oxide, a non-hydrated green chromium oxide, Prussian blue, a cobalt aluminate, cobalt blue, manganese violet, a mica-titanium, bismuth oxychloride, zinc oxide, cerium oxide, zirconium oxide and a mixture thereof, said fatty binder being at least one of an oil, a wax or a mixture thereof.

24. An anhydrous cosmetic composition for the skin consisting of a dispersion of solid particles in a fatty binder, at least one portion of said solid particles having a solid surface coated with one or more cationic polymer, present in an amount of from 0.1 percent to 10 percent by weight relative to the total weight of said coated particles, said cationic polymer containing quaternary ammonium groups as part of the polymer chain or as a side substituent, wherein said solid particles are at least one of an inorganic filler selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide, an aerogel, and an inorganic pigment selected from the group consisting of titanium dioxide, zinc oxide, a colored natural or synthetic black iron oxide, a hydrated green chromium oxide, a non-hydrated green chromium oxide, Prussian blue, a cobalt aluminate, cobalt blue, manganese violet, a mica-titanium, bismuth oxychloride, zinc oxide, cerium oxide, zirconium oxide and a mixture thereof, said fatty binder being at least one of an oil, a wax or a mixture thereof;

said composition optionally also consisting of D & C pigment No. 5, D & C pigment No. 7, D & C pigment No. 34, zinc stearate or nylon powder.

25. The cosmetic composition of claim 17 wherein said coated particles comprise an inorganic filler or an inorganic pigment.

26. The cosmetic composition of claim 17 wherein said cationic polymer is an acrylic, vinyl, siliconized, fluorinated or saccharide polymer.

27. The composition of claim 25 wherein said inorganic filler is selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide and an aerogel.

28. The composition of claim 25 wherein said inorganic pigment is selected from the group consisting of titanium dioxide, zinc oxide, a colored natural or synthetic black iron oxide, a colored neutral or synthetic red iron oxide, a colored natural or synthetic yellow iron oxide, a hydrated green chromium oxide, a non-hydrated green chromium oxide, Prussian blue, an ultramarine pigment, a cobalt aluminate, cobalt blue and manganese violet.

29. The composition of claim 25 wherein said inorganic pigment is selected from the group consisting of a mica-titanium and bismuth oxychloride.

30. The composition of claim 25 wherein said inorganic pigment is selected from the group consisting of zinc oxide, cerium oxide, zirconium oxide and mixtures thereof.

31. The cosmetic composition of claim 24 wherein said solid coated particles contain less than 8 percent by weight of cationic polymer.

32. The composition of claim 24 wherein said inorganic pigment is selected from the group consisting of titanium dioxide, zinc oxide, a colored natural or synthetic black iron oxide, a colored neutral or synthetic red iron oxide, a colored natural or synthetic yellow iron oxide, a hydrated green chromium oxide, a non-hydrated green chromium oxide, Prussian blue, an ultramarine pigment, a cobalt aluminate, cobalt blue and manganese violet.

33. The composition of claim 24 wherein said inorganic pigment is selected from the group consisting of a mica-titanium and bismuth oxychloride.

34. The composition of claim 24 wherein said inorganic pigment is selected from the group consisting of zinc oxide, cerium oxide, zirconium oxide and mixtures thereof.

35. A cosmetic treatment process for coloring nails consisting essentially of applying to said nails a nail varnish composition consisting essentially of solid particles in a binder comprising a solution of a film forming polymer and a plasticizer in an organic solvent, at least one portion of said solid particles having a solid surface coated with one or more cationic polymer, present in an amount of from 0.1 percent to 10 percent by weight relative to the total weight of said coated particles, said cationic polymer containing quaternary ammonium groups as part of the polymer chain or as a side substituent, said cationic polymer being an acrylic, vinyl, siliconized, fluorinated or saccharide polymer, wherein said solid particles are at least one of an inorganic filler selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide, an aerogel, and an inorganic pigment selected from the group consisting of titanium dioxide, zinc oxide, a colored natural or synthetic black iron oxide, a hydrated green chromium oxide, Prussian blue, a cobalt aluminate, cobalt blue, manganese violet, a mica-titanium, bismuth oxychloride, zinc oxide, cerium oxide, zirconium oxide and a mixture thereof.

36. An anhydrous nail varnish composition consisting of a dispersion of solid particles in a binder comprising film forming polymer and a plasticizer in an organic solvent, at least one portion of said solid particles having a solid surface coated with at least one cationic polymer, present in an amount of from 0.1 percent to 10 percent by weight relative to the total weight of said coated particles, said cationic polymer containing quaternary ammonium groups as a part of the polymer chain or as a side substituent; said particles being selected from the group consisting of calcium carbonate, aluminum silicate, kaolin, calcium silicate, sodium aluminosilicate, magnesium silicate, talc, potassium aluminosilicate, mica, hydrogenated magnesium aluminosilicate, barium sulphate, calcium sulphate, precipitated silicon dioxide, pyrogenic silicon dioxide, an aerogel, titanium dioxide, zinc oxide, a colored natural or synthetic black iron oxide, a colored neutral or synthetic red iron oxide, a colored natural or synthetic yellow iron oxide, a hydrated green chromium oxide, a non-hydrated green chromium oxide, Prussian blue, an ultramarine pigment, a cobalt aluminate, cobalt blue, manganese violet, a mica-titanium, bismuth oxychloride, cerium oxide, zirconium oxide and mixtures thereof; and said cationic polymer being an acrylic, vinyl, siliconized, fluorinated or saccharide polymer.

* * * * *